United States Patent
Altshuler et al.

(10) Patent No.: US 11,617,858 B2
(45) Date of Patent: Apr. 4, 2023

(54) ERGONOMIC STEERING HANDLE

(71) Applicant: IPG PHOTONICS CORPORATION, Oxford, MA (US)

(72) Inventors: Gregory Altshuler, Lincoln, MA (US); Ilya Yaroslavsky, N. Andover, MA (US); Dmitri Boutoussov, Southborough, MA (US); Viktoriya Andreeva, Moscow Region (RU); Olivier Traxer, Paris (FR); Michael Barenboym, Boston, MA (US); Isaac Ostrovsky, Wellesley, MA (US); Anastasiya Kovalenko, Moscow Region (RU)

(73) Assignee: IPG PHOTONICS CORPORATION, Oxford, MA (US)

( * ) Notice: Subject to any disclaimer, the term of this patent is extended or adjusted under 35 U.S.C. 154(b) by 0 days.

(21) Appl. No.: 17/423,943

(22) PCT Filed: Jan. 20, 2020

(86) PCT No.: PCT/US2020/014285
§ 371 (c)(1),
(2) Date: Dec. 14, 2021

(87) PCT Pub. No.: WO2020/150709
PCT Pub. Date: Jul. 23, 2020

(65) Prior Publication Data
US 2022/0152353 A1     May 19, 2022

Related U.S. Application Data

(60) Provisional application No. 62/868,105, filed on Jun. 28, 2019, provisional application No. 62/794,328, filed on Jan. 18, 2019.

(51) Int. Cl.
*A61M 25/01*     (2006.01)
*G05G 1/10*     (2006.01)

(52) U.S. Cl.
CPC ........... *A61M 25/0136* (2013.01); *G05G 1/10* (2013.01); *A61M 2205/586* (2013.01)

(58) Field of Classification Search
CPC ........ A61M 25/0136; A61M 2205/586; A61M 1/77; A61M 1/92; A61M 1/73; A61B 17/320016; G05G 1/10
See application file for complete search history.

(56) References Cited

U.S. PATENT DOCUMENTS

| | | |
|---|---|---|
| 2,995,336 A | 8/1961 | Usab |
| 2,995,337 A | 8/1961 | Tanner |

(Continued)

FOREIGN PATENT DOCUMENTS

| | | |
|---|---|---|
| EP | 537573 A2 | 4/1993 |
| JP | 2011-239989 A | 12/2011 |

(Continued)

OTHER PUBLICATIONS

Freudenberg Medical MIS Medical Brochure "Medical Device Solutions" Freudenberg Medical Minimally Invasive Solutions (Oct. 2017) 11 pages.

(Continued)

*Primary Examiner* — Laura A Bouchelle
(74) *Attorney, Agent, or Firm* — Caroline J. Roush, Esq.

(57) ABSTRACT

Catheter steering handles that are ergonomically designed to enable an operator to reduce hand fatigue. Various ergonomic aspects of the disclosed steering handles include geometries that more naturally conform to the palm of the hand and that enable the hand to be held in a natural, low stress posture during operation of the steering handle. In another aspect of the disclosure, the catheter steering handle (Continued)

is configured so that the operator can release or partially release the grip on the handle, thereby enabling the operator to relax and flex the hand, thereby reducing fatigue.

16 Claims, 9 Drawing Sheets

(56) References Cited

U.S. PATENT DOCUMENTS

| | | | |
|---|---|---|---|
| 4,146,019 A | 3/1979 | Bass et al. | |
| 4,270,525 A | 6/1981 | Furihata | |
| 4,402,310 A | 9/1983 | Kimura | |
| 4,617,915 A * | 10/1986 | Arakawa | A61B 1/042 |
| | | | 600/102 |
| 5,186,714 A | 2/1993 | Boudreault et al. | |
| 5,207,213 A | 5/1993 | Auhll et al. | |
| 5,242,387 A | 9/1993 | Loughlin | |
| 5,288,290 A | 2/1994 | Brody | |
| 5,322,064 A | 6/1994 | Lundquist | |
| 5,338,314 A | 8/1994 | Ryan | |
| 5,380,277 A | 1/1995 | Phillips | |
| 5,409,013 A | 4/1995 | Clement | |
| 5,505,210 A | 4/1996 | Clement | |
| 5,797,907 A | 8/1998 | Clement | |
| 5,916,193 A | 6/1999 | Stevens et al. | |
| 6,083,205 A | 7/2000 | Bourne et al. | |
| 6,090,103 A | 7/2000 | Hakky et al. | |
| 6,152,919 A | 11/2000 | Hakky | |
| 6,551,302 B1 | 4/2003 | Rosinko et al. | |
| 8,303,581 B2 | 11/2012 | Arts et al. | |
| 8,636,651 B2 | 1/2014 | Deal | |
| 8,827,899 B2 | 9/2014 | Farr et al. | |
| 9,393,033 B2 | 7/2016 | Zerfas et al. | |
| 9,713,700 B2 | 7/2017 | Chang et al. | |
| 9,723,973 B2 * | 8/2017 | Dillon | A61B 1/0125 |
| 9,775,675 B2 | 10/2017 | Irby, III | |
| 9,974,938 B2 | 5/2018 | Pepin et al. | |
| 10,004,560 B2 | 6/2018 | Zerfas et al. | |
| 2003/0130575 A1 | 7/2003 | Desai | |
| 2005/0096646 A1 * | 5/2005 | Wellman | A61B 17/22031 |
| | | | 606/171 |
| 2008/0188868 A1 | 8/2008 | Weitzner et al. | |
| 2010/0168519 A1 | 7/2010 | Matsuo | |
| 2011/0202039 A1 | 8/2011 | Schaaf | |
| 2012/0209074 A1 | 8/2012 | Titus | |
| 2014/0213848 A1 | 7/2014 | Moskowitz et al. | |
| 2015/0196361 A1 | 7/2015 | Preiss et al. | |
| 2015/0305759 A1 | 10/2015 | St. George et al. | |
| 2016/0166320 A1 | 6/2016 | Ciulla et al. | |
| 2017/0215899 A1 | 8/2017 | Harrah et al. | |
| 2017/0215964 A1 | 8/2017 | Harrah et al. | |
| 2017/0340191 A1 | 11/2017 | Zeng et al. | |
| 2018/0008766 A1 | 1/2018 | Scheller et al. | |
| 2020/0054194 A1 * | 2/2020 | Melsheimer | A61B 1/0052 |

FOREIGN PATENT DOCUMENTS

| | | |
|---|---|---|
| WO | WO 1993/014700 | 8/1993 |
| WO | WO 1996/032895 | 10/1996 |
| WO | WO 2011/142994 A2 | 11/2011 |
| WO | 2017/212332 A1 | 12/2017 |

OTHER PUBLICATIONS

Products Flashcards "Study Blue" (2018) downloaded at http://www.studyblue.com/about/legal.
International Search Report for Application No. PCT/US2020/014282, dated Sep. 10, 2020, 2 pages.
Rocamed Products Catalog (2018), Products Catalogue MKG-CT-EN-2018-00 (2018) downloaded at www.rocamed.com 81 pages.
Lynn Hadaway, The Art and Science of Infusion Nursing "Stopcocks for Infusion Therapy" Evidence and Experience, Infusion Nurses Society, Journal of Infusion Nursing (2018) 34 pages.

* cited by examiner

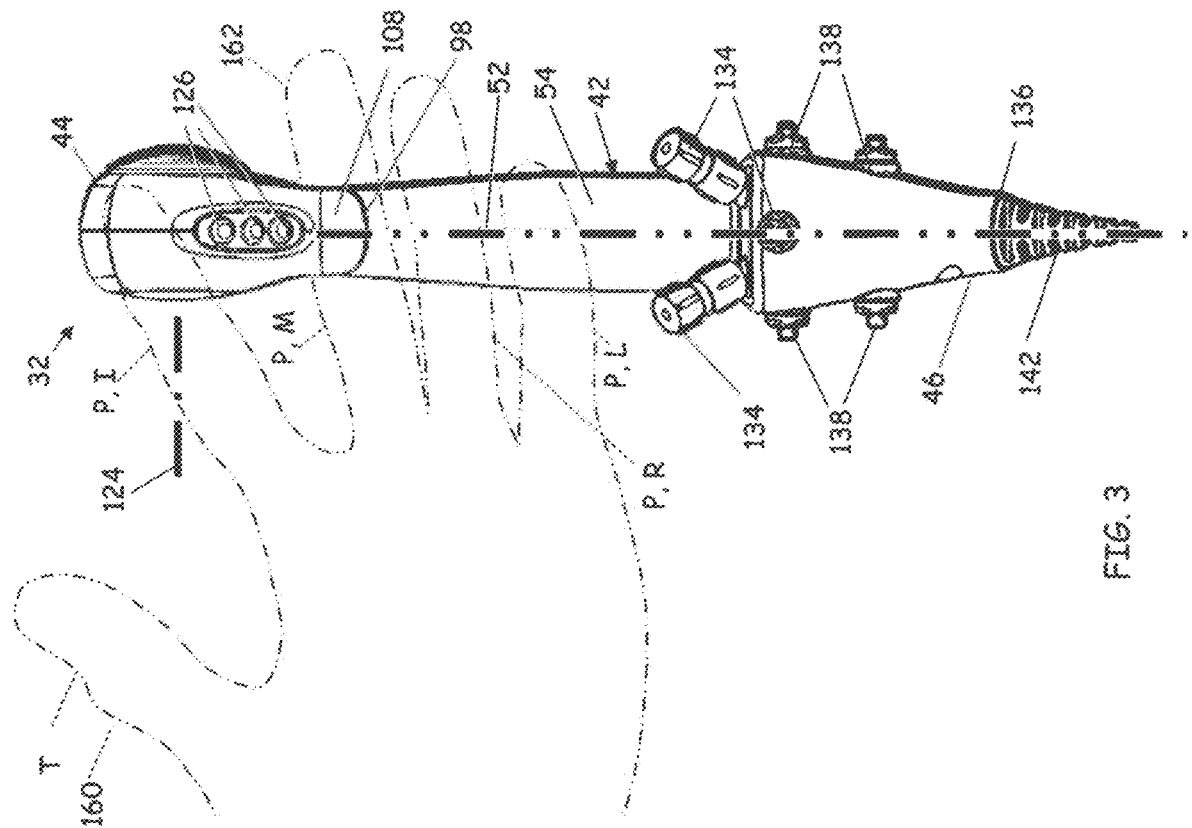
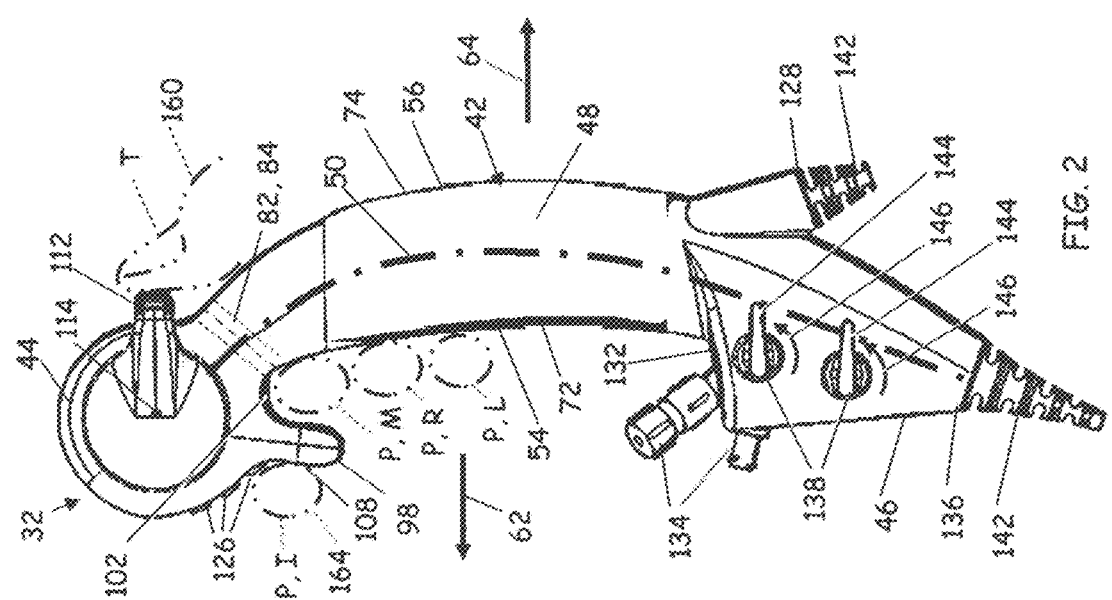

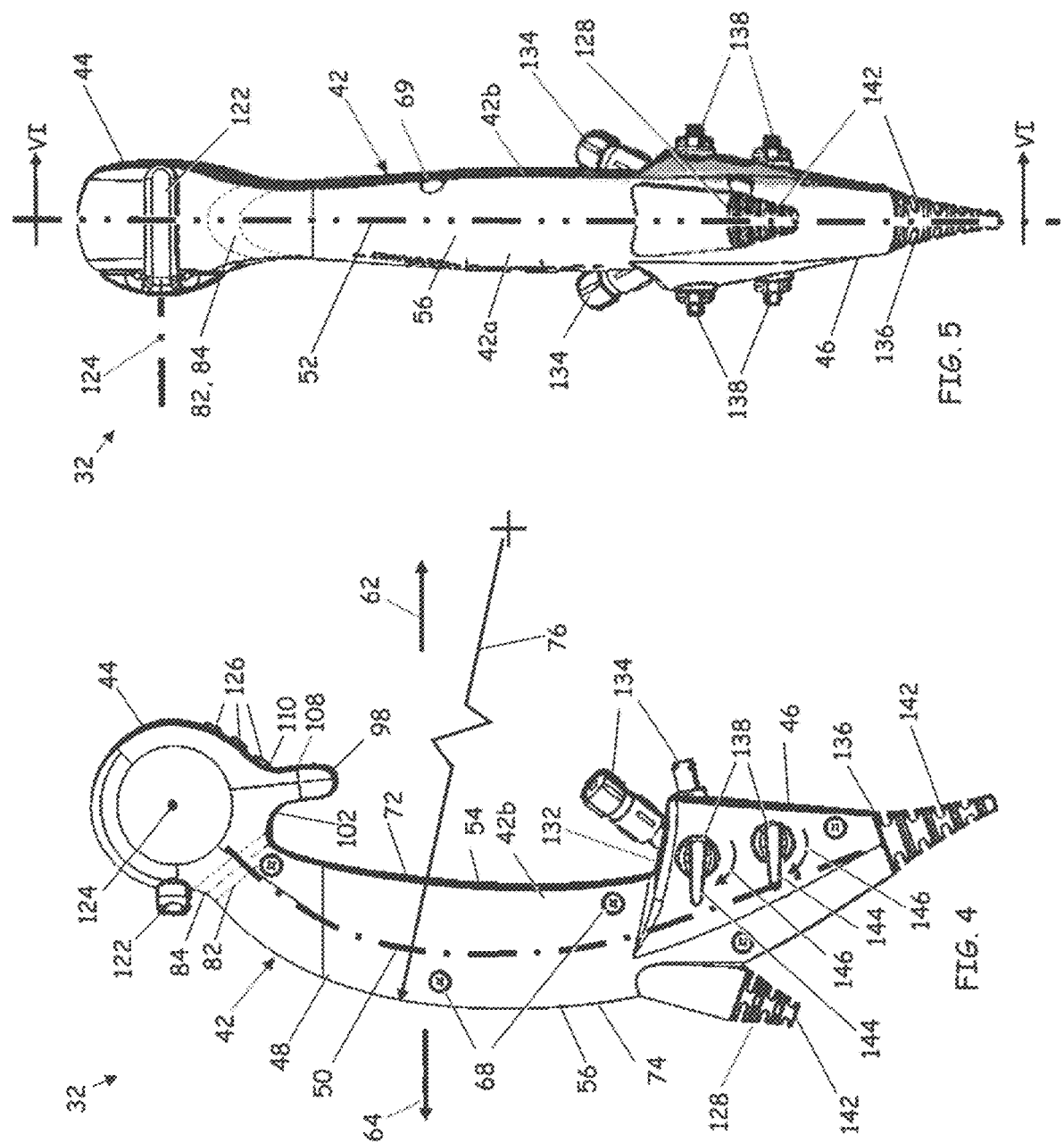

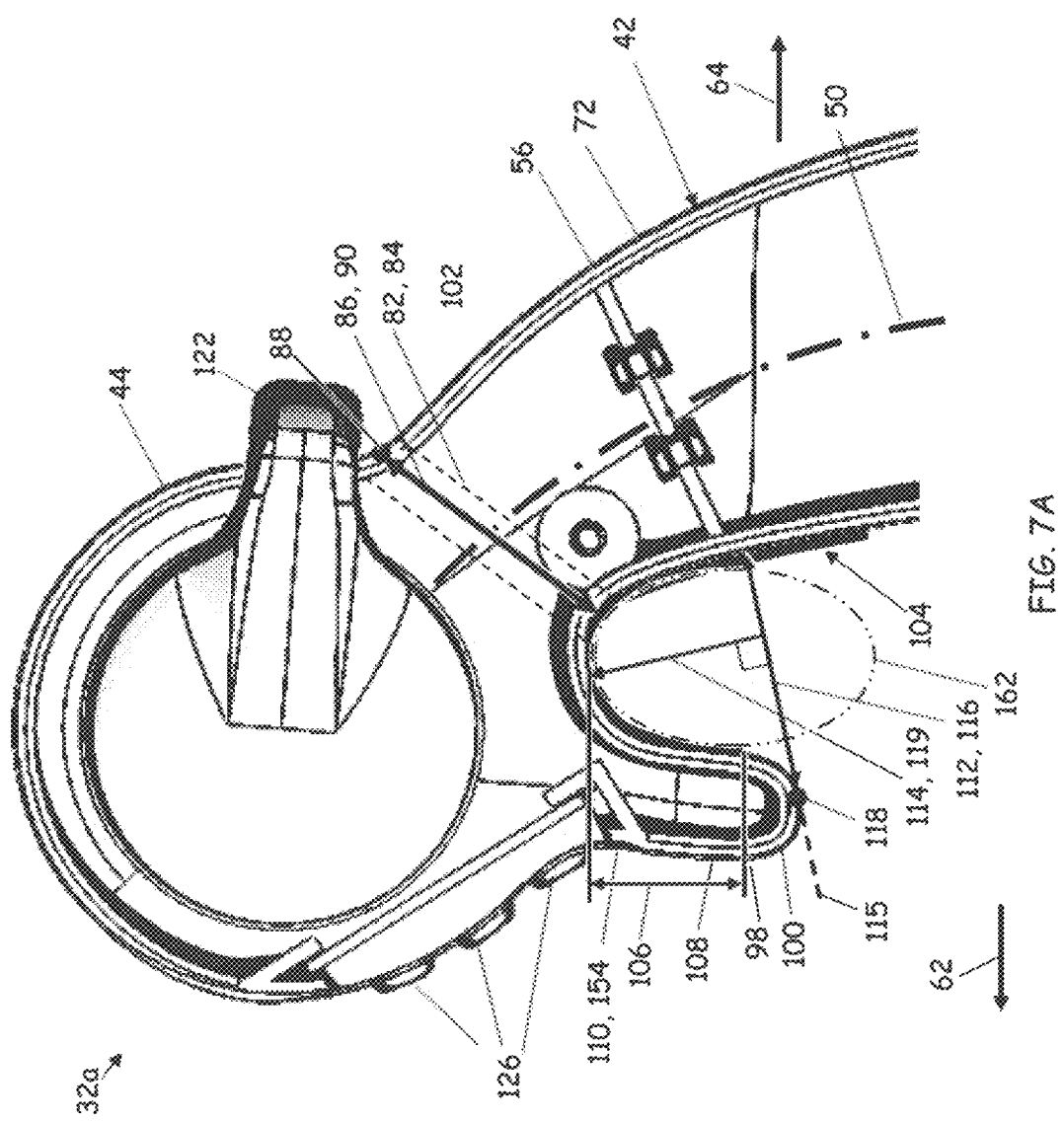

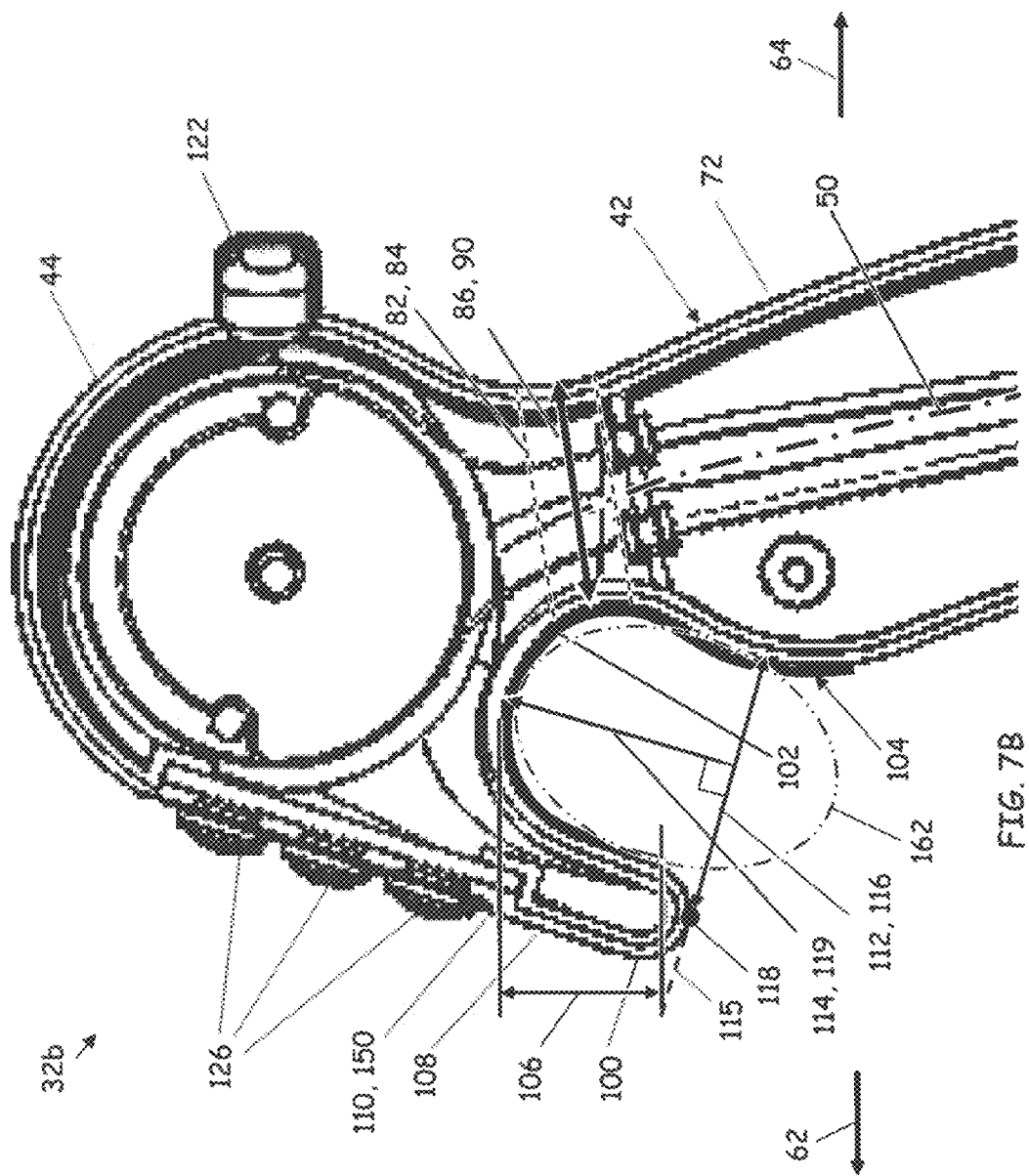

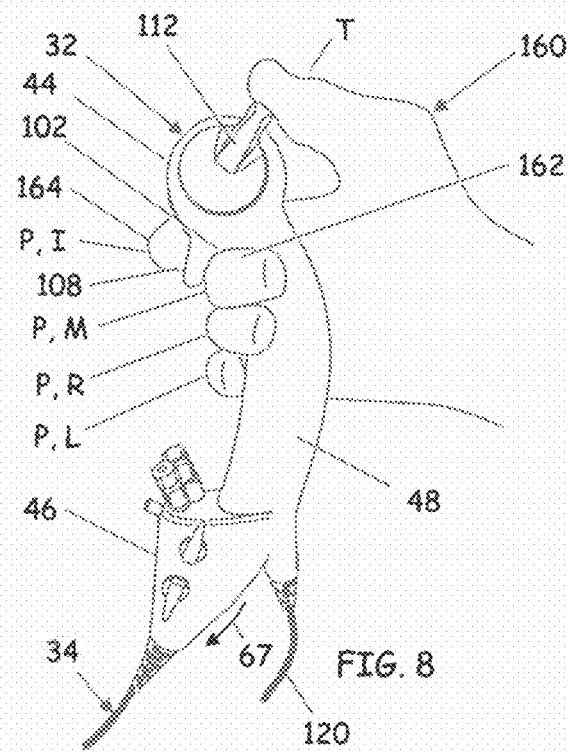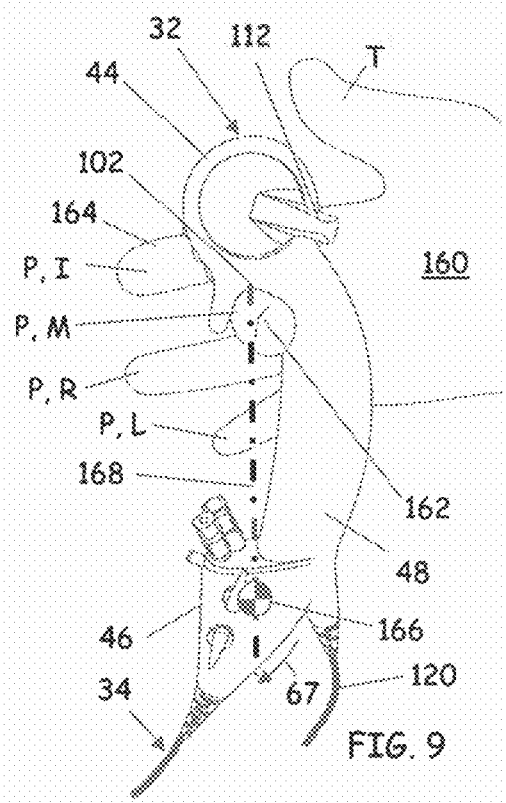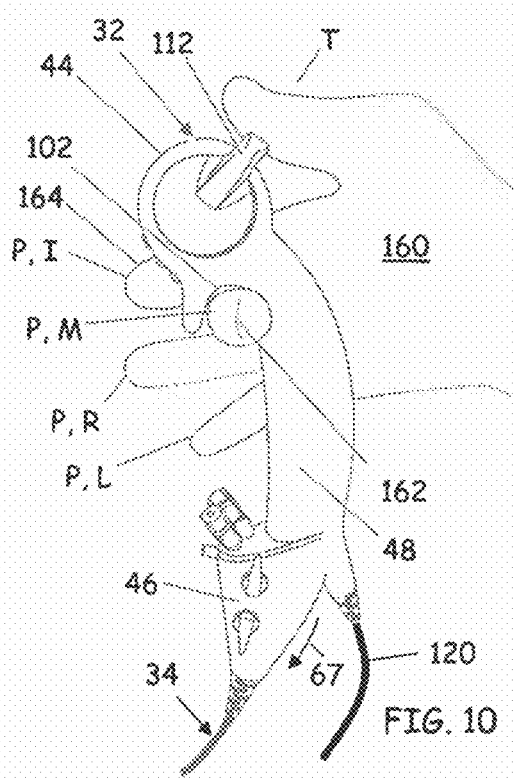

ERGONOMIC STEERING HANDLE

RELATED APPLICATIONS

This application claims the benefit of U.S. Provisional Patent Application No. 62/794,328, filed Jan. 18, 2019, and of U.S. Provisional Patent Application No. 62/868,105, filed Jun. 28, 2019, the disclosures of which are hereby incorporated by reference herein in their entirety.

FIELD OF THE DISCLOSURE

This application is directed generally to steering handles for flexible catheters and more specifically to steering handle forms that ergonomically enhance the gripping of the handle.

BACKGROUND OF THE DISCLOSURE

Steering handles are used to deflect the distal end of a flexible catheter while directing the catheter through bodily organs, and to control the functions of the catheter once the catheter is in place. Examples include vascular access to the heart and ureter access to the kidney. A common issue with operation of steering handles is hand fatigue of the operator. Often, the operator must hold the steering handle with the hand in a more or less fixed position for extended periods during these procedures. A steering handle that addresses the problem of hand fatigue would be welcomed.

SUMMARY OF THE DISCLOSURE

Various embodiments of the disclosure present catheter steering handles that are ergonomically designed to enable an operator to reduce hand fatigue. Various ergonomic aspects of the disclosed steering handles include geometries that more naturally conform to the palm of the hand and that enable the hand to be held in a natural, low stress posture during operation of the steering handle. In another aspect of the disclosure, the catheter steering handle is configured so that the operator can release or partially release the grip on the handle, thereby enabling the operator to relax and flex the hand, thereby reducing fatigue.

Structurally, various embodiments of the disclosure include a steering handle for a flexible catheter, comprising a housing including a body portion defining a handle axis and a head portion and a base portion separated by the body portion along the handle axis, the housing defining a mid-plane that is coplanar with the handle axis and passes through a forward side and a rearward side of the housing, a thumb lever coupled to the head portion, the thumb lever being rotatable about a lateral axis that is orthogonal to the mid-plane. The thumb lever may extend in a rearward direction and parallel to the mid-plane and may be rotatable about a lateral axis that is orthogonal to the mid-plane.

In some embodiments, the housing defines a transition portion at a junction between the body portion and the head portion, the housing having a cross-section about the handle axis at the transition portion that defines a junction dimension coplanar with the mid-plane that is reduced relative to the head portion and the body portion at the mid-plane immediately adjacent the transition portion. The junction dimension may be in a range of 20 millimeters to 30 millimeters inclusive.

In some embodiments, the handle axis is curvilinear, wherein the rearward side of the body portion defines a convex profile at the mid-plane, and wherein the forward side of the body portion defines a concave profile at the mid-plane. The convex profile and the concave profile may define a radius in a range of 300 millimeters to 1000 millimeters inclusive.

The head portion and the transition portion may define a catch on the forward side of the housing at the mid-plane. The forward side of the head portion may include a protrusion that extends in a forward direction to form the catch. In some embodiments, at least a portion of the protrusion provides a finger rest. In some embodiments, the head portion and the transition portion define a hook profile on the forward side of the housing at the mid-plane. The forward side of the head portion may include a protrusion that extends in a forward direction and defines a front length of the hook profile. At least a portion of the protrusion may provide a finger rest. In some embodiments, at least one push button actuator is disposed proximate the finger rest.

In some embodiments, the catch defines a hook profile at the mid-plane. The catch may define an opening at the mid-plane, the opening being defined along a reference line that defines a minimum opening dimension from the forward side of the body portion of the handle to a reference point an a distal end portion of the protrusion. In some embodiments, the catch defines a depth at the mid-plane, the depth being defined as a maximum depth dimension from the reference line to the hook profile that is perpendicular to the reference line. In some embodiments, the minimum opening dimension is within a range of 20 millimeters to 30 millimeters inclusive; in some embodiments, the minimum opening dimension is within a range of 24 millimeters to 27 millimeters inclusive. In some embodiments, the maximum depth dimension is within a range of 13 millimeters to 28 millimeters inclusive; in some embodiments, the maximum depth dimension is within a range of 18 millimeters to 23 millimeters inclusive. In some embodiments, a ratio of the minimum opening dimension to the maximum depth dimension is within a range of 0.7 to 1.7 inclusive; in some embodiments, the ratio of the minimum opening dimension to the maximum depth dimension is within a range of 0.9 to 1.5 inclusive; in some embodiments, the ratio of the minimum opening dimension to the maximum depth dimension is within a range of 1.1 to 1.4 inclusive.

The base portion may include a bulkhead. In some embodiments, an exterior surface of the bulkhead is centered about a bulkhead plane, the bulkhead plane intersecting the body portion of the handle at the forward side of the housing to define a junction point on the mid-plane, the bulkhead plane defining an acute slope angle that extends distally from a reference vector that is normal to the forward side of the housing at the junction point. In some embodiments, the acute slope angle is within a range of 10 degrees to 60 degrees inclusive; in some embodiments, the acute slope angle is within a range of 15 degrees to 50 degrees inclusive; in some embodiments, the acute slope angle is within a range of 20 degrees to 40 degrees inclusive.

In various embodiments of the disclosure, a catheter assembly comprises a housing including a head portion at a proximal end of the housing, a base portion at a distal end of the housing, a body portion that separates the head portion from the base portion, the body portion defining a handle axis, the housing defining a mid-plane that is coplanar with the handle axis and passes through a forward side and a rearward side of the housing, a catheter port, and an electrical port. The handle axis may be curvilinear. A catheter is coupled to and extends distally from the catheter port, and an electrical cable is coupled to and extending from the electrical port. The catheter may be a flexible catheter. The housing defines a transition portion at a junction between the body portion and the head portion, the head portion and the transition portion defining a catch on the forward side of the housing at the mid-plane. In some embodiments, the catheter port extends from a distal extremity of the base portion. The electrical port may extend from the base portion. In some embodiments, the forward side of the head portion includes a protrusion that extends in a forward direction to form the catch. At least a portion of the protrusion may provide a finger rest. In some embodiments, at least one push button actuator is disposed on a proximal portion of the protrusion portion.

In some embodiments, the housing defines a cross-section about the handle axis at the transition portion that defines a junction dimension coplanar with the mid-plane that is reduced relative to the head portion and the body portion at the mid-plane immediately adjacent the transition portion. The junction dimension may be in a range of 20 millimeters to 30 millimeters inclusive. In some embodiments, the rearward side of the body portion defines a convex profile at the mid-plane. The forward side of the body portion may define a concave portion at the mid-plane. In some embodiments, a thumb lever is coupled to the head portion, the thumb lever being rotatable about a lateral axis that is orthogonal to the mid-plane. The thumb lever may extend in a rearward direction and parallel to the mid-plane.

In various embodiments of the disclosure, a method of relieving hand fatigue while operating a catheter steering handle is disclosed, comprising: grasping a body portion of the catheter steering handle between a palm and phalanges of a hand, with a first of the phalanges of the hand being within a hook profile defined by the catheter steering handle; articulating a thumb lever of the catheter steering handle with a thumb of the hand to steer the flexible catheter; and opening the hand to release the body portion of the catheter steering handle with the hook profile of the catheter steering handle passing over the first of the phalanges so that the catheter steering handle hangs from the first of the phalanges. The method may include resting a second of the phalanges on a finger rest portion of a protrusion of the head that extends in a forward direction. In some embodiments, the body portion of the catheter steering handle provided in the step of providing a catheter steering handle is an arcuate body portion, the phalanges grasping a concave face of the arcuate body portion during the step of grasping, the palm resting on a convex face of the arcuate body portion during the step of grasping, the convex face being opposite the concave face. In some embodiments, a base portion of the handle is vertically aligned below the first of the phalanges during the step of opening the hand. A center of gravity of the handle may be vertically aligned below the first of the phalanges during the step of opening the hand. In some embodiments, the method includes providing a catheter steering handle operatively coupled to a flexible catheter, and providing various steps of the method as operating instructions on a tangible, non-transitory medium.

BRIEF DESCRIPTION OF THE DRAWINGS

FIG. 2 is a left side elevational view the catheter steering handle of FIG. 1 according to an embodiment of the disclosure;

FIG. 3 is a front elevational view of the catheter steering handle of FIG. 1 according to an embodiment of the disclosure;

FIG. 4 is a right side elevational view of the catheter steering handle of FIG. 1 according to an embodiment of the disclosure;

FIG. 5 is a rear elevational view of the catheter steering handle of FIG. 1 according to an embodiment of the disclosure;

FIG. 7A is an enlarged, partial view of FIG. 6A at inset VIIA according to an embodiment of the disclosure;

FIG. 7B is an enlarged, partial view of FIG. 6B at inset VIIB according to an embodiment of the disclosure;

FIG. 8 is a perspective view of a catheter steering handle being held in a grasped posture according to an embodiment of the disclosure; and FIGS. 9 and 10 are perspective views of the catheter steering handle of FIG. 8 being held in relaxed postures according to an embodiment of the disclosure.

DETAILED DESCRIPTION OF THE DRAWINGS

Figure 1A:
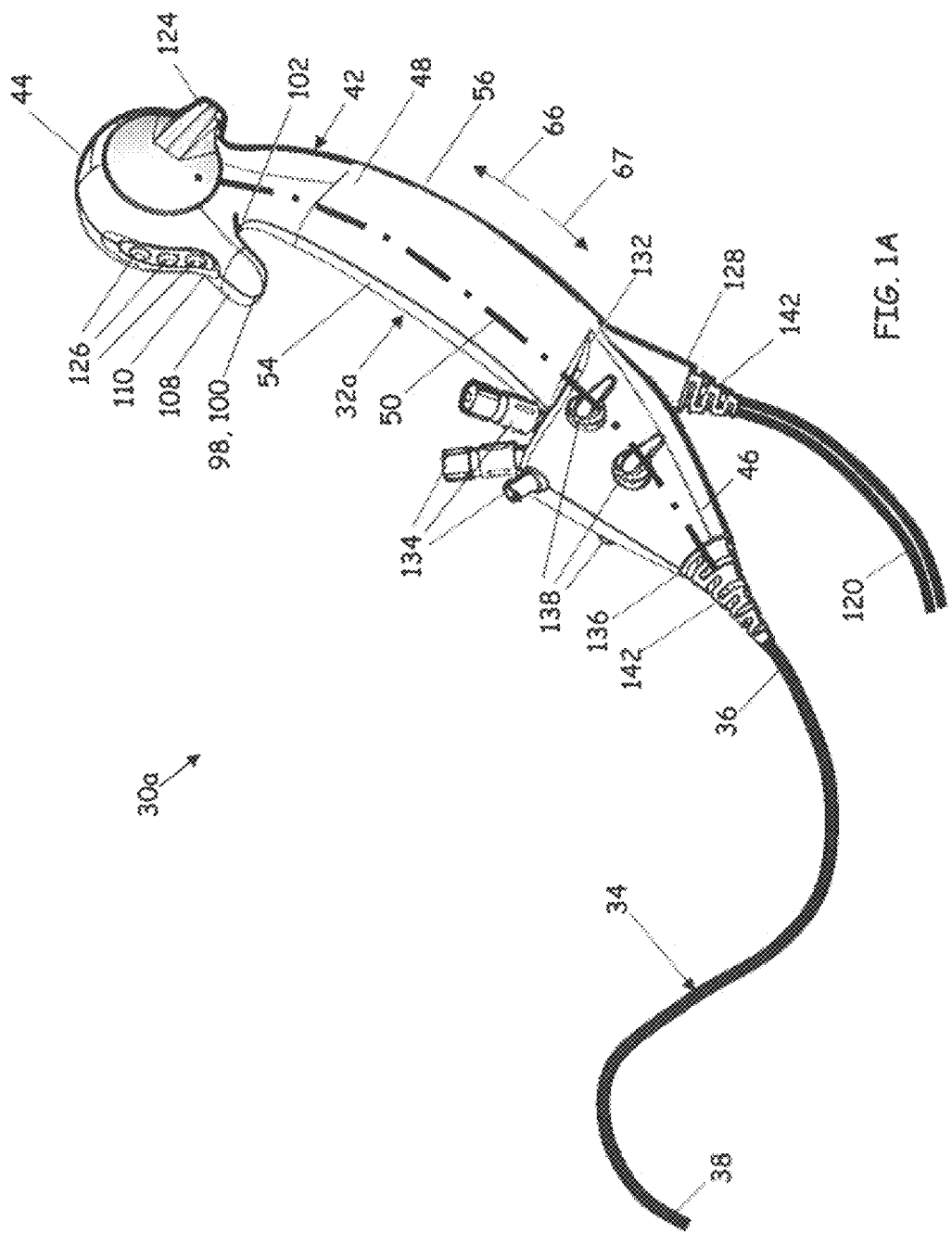
FIGS. 1A and 1B are perspective views of a catheter assembly having a catheter steering handle coupled to a steerable catheter according to embodiments the disclosure.

Referring to FIGS. 1A through 7B, catheter assemblies 30a and 30b including steering handles 32a and 32b, respectively, are depicted according to embodiments of the disclosure. Herein, the individual catheter assemblies 30a and 30b and steering handles 32a and 32b are referred to generically and collectively as catheter assembly or assemblies 30 and steering handle or handles 32. The catheter assemblies 30 include a steerable catheter 34 having a proximal end portion 36 and a distal end portion 38. The catheter steering handle 32 includes a housing 42 having a head portion 44 and a base portion 46 separated by a body portion 48, the body portion 48 defining a handle axis 50 along which the head portion 44, body portion 48, and base portion 46 are arranged. The housing 42 defines a mid-plane 52 that is coplanar with the handle axis 50 and passes through a forward side 54 and a rearward side 56 of the housing 42. The forward side 54 of the housing 42 faces in a forward direction 62 and the rearward side 56 of the housing 42 faces in a rearward direction 64.

Herein, in the context of the steering handles 32 and the catheter 34, "proximal" and "proximally" refer to a direction 66 along the handle axis 50 that is toward the head portion 44, whereas "distal" and "distally" refer to a direction 67 along the handle axis 50 that is away from the head portion 44. Accordingly, the head portion 44 is proximal to the body portion 48 of the steering handle 32 and the base portion is distal to the body portion 48 of the steering handle 32.

In some embodiments, the housing 42 is bifurcated at the mid-plane 52 to define two housing portions 42a and 42b (FIGS. 4 and. 5). The housing portions 42a and 42b may be secured together with fasteners 68. In some embodiments, the fasteners 68 are mounted with the heads recessed within counter bores 69. The counter bores 69 may be located on the same housing portion 42a, 42b (depicted on housing portion 42b in FIG. 4). It is contemplated that the housing portions 42a and 42b could be joined without fasteners, for example with press fit structures that extend between the housing portions 42a and 42b.

The body portion 48 may be curved, with the forward side 54 defining a concave profile 72 and the rearward side 56 defining a convex profile 74 at the mid-plane 52. In such embodiments, the body portion 48 defines the handle axis 50 as curvilinear. In some embodiments, the convex profile 74 defines a radius 76 (FIGS. 4 and 6B) in a range of 100 millimeters to 500 millimeters inclusive; in some embodiments, the convex profile 74 defines a radius 76 in a range of 125 millimeters to 400 millimeters inclusive; in some embodiments, the convex profile 74 defines a radius 76 in a range of 100 millimeters to 300 millimeters inclusive. Herein, a range that is said to be "inclusive" includes the endpoint values of the stated range as well as all values between the endpoint values.

The housing 42 defines a transition portion 82 at a junction 84 between the head portion 44 and the body portion 48. The housing 42 defines a cross-section 86 about the handle axis 50 at the transition portion 82. A local minima 88 is defined at the transition portion 82 on the rearward side 56 of the handle 42 at the mid-plane 52 (FIGS. 7A and 7B). A junction dimension 90 is defined as the minimum dimension between local minima 88 and the forward side 54 steering handle 32 at the mid-plane 52. The junction dimension 90 may be reduced relative to the mid-plane dimensions of the head portion 44 and the body portion 48 immediately adjacent the transition portion 82. In some embodiments, the junction dimension 90 is in a range of 20 millimeters to 30 millimeters inclusive.

The forward side 54 of the head portion 44 includes a protrusion 98 that extends partially over the body portion 48 in the forward direction 62, the protrusion including a distal end portion 100. The body portion 48 and the protrusion 98 of the head portion 44 combine to define a catch 102 that is configured for insertion of a phalange P of the hand. In some embodiments, the catch 102 defines a hook profile 104 (traced at FIG. 7) at the mid-plane 52 of the transition portion 82 on the forward side 54 of the housing 42. The protrusion 98 defines a front length 106 of the hook profile 104. The head portion 44 defines a forward face or contour 110 at the protrusion 98. In some embodiments, at least a portion of the protrusion 98 also provides a finger rest 108.

The catch 102 may also be characterized as defining an opening 112 and a depth 114 at the mid-plane 52. The opening 112 is defined along a reference line 115 that defines a minimum opening dimension 116 from the forward side 54 of the body portion 48 of the handle 32 to a reference point 118 on the distal end portion 100, the reference line 115 being tangential to the reference point 118. The depth 114 is defined as a maximum depth dimension 119 from the hook profile 104 of the catch 102 to the reference line 115, the maximum depth dimension 119 being perpendicular to the reference line 115.

In some embodiments, a ratio of the minimum opening dimension 116 to the maximum depth dimension 119 is within a range of 0.7 to 1.7 inclusive; in some embodiments, the ratio of the minimum opening dimension 116 to the maximum depth dimension 119 is within a range of 0.9 to 1.5 inclusive; in some embodiments, the ratio of the minimum opening dimension 116 to the maximum depth dimension 119 is within a range of 1.1 to 1.4 inclusive. In some embodiments, the minimum opening dimension 116 is within a range of 20 millimeters to 30 millimeters inclusive; in some embodiments, the minimum opening dimension 116 is within a range of 24 millimeters to 27 millimeters inclusive. In some embodiments, the maximum depth dimension 119 is within a range of 13 millimeters to 28 millimeters inclusive; in some embodiments, the maximum depth dimension 119 is within a range of 18 millimeters to 23 millimeters inclusive.

In some embodiments, the head portion 44 includes a thumb lever 122. The thumb lever 122 extends in the rearward direction 64 and parallel to the mid-plane 52 and is used for articulating the distal end portion 38 of the steerable catheter 34. The thumb lever 122 is bi-directionally rotatable about a lateral axis 124 that is orthogonal to the mid-plane 52. The head portion 44 may also include one or more push button actuators 126 opposite the thumb lever 122. The push button actuator(s) 126 may be disposed on the head portion 44 proximate the finger rest 108.

In some embodiments, the catheter steering handle 32 includes an electrical port 128 through which a cable or wiring 120 is routed. The cable 120 may be utilized, for example, for controlling illumination from the LEDs, receiving signals from an imaging device, providing control commands from the push button actuator(s) 126, and supplying power to the catheter assembly 30. In some embodiments, both the catheter 34 and the cable 120 extend generally proximal to the catheter steering handle 32.

The base portion 46 may include a bulkhead 132 through which one or more input ports 134 are interfaced with external systems (e.g., irrigation, aspiration, or fiber optic systems). Some or all of the input ports 134 may be optionally configured for compatibility with LUER taper fittings. In some embodiments, some or all of the input ports 134 are fitted with an external valve such as a stopcock valve (not depicted). The base portion 46 may include a catheter port 136 to which the proximal end portion 36 of the steerable catheter 34 may be coupled. One or both of the electrical port 128 and the catheter port 136 may be fitted with a strain relief structure(s) 142.

Figure 6A:
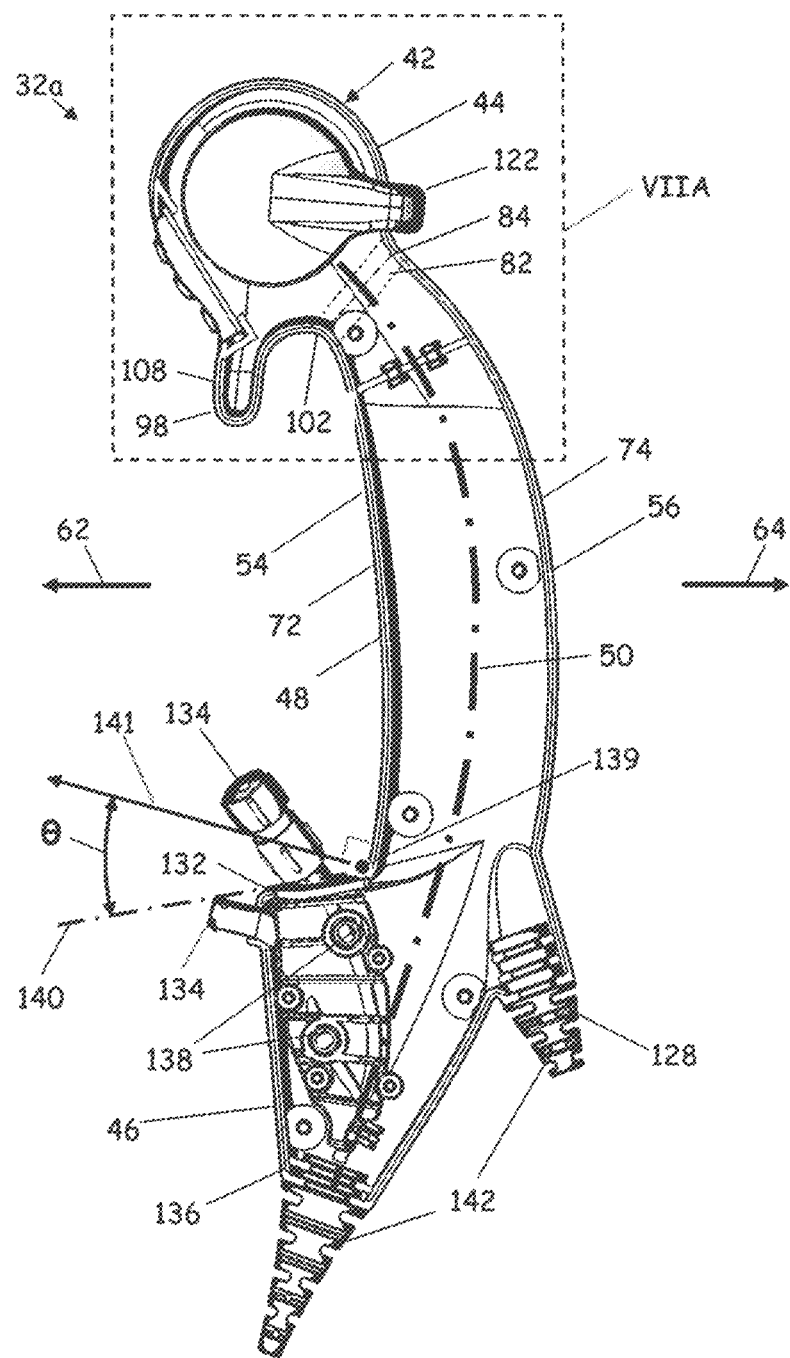
FIG. 6A is a partial sectional view along mid-plane VI-VI of FIG. 5 according to an embodiment of the disclosure.
Figure 6B:
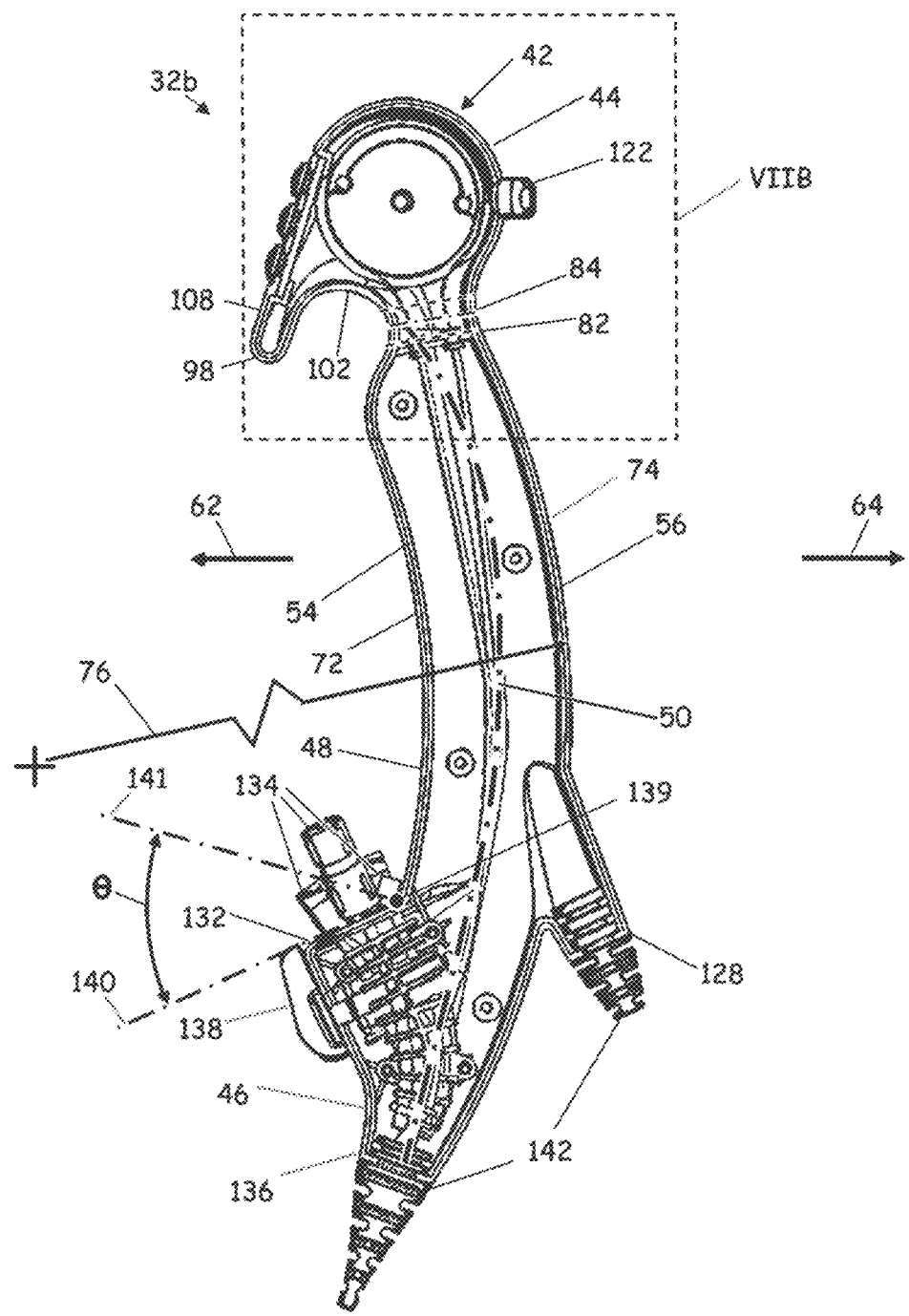
FIG. 6B is a sectional view along a mid-plane of the catheter assembly of FIG. 1B according to an embodiment of the disclosure.

The bulkhead 132 intersects the forward side 54 of the body portion 48 at a junction point 139 located at the mid-plane 52 of the handle 32 (FIGS. 6A and 6B). An exterior surface of the bulkhead 132 may be centered about a bulkhead plane 140 that extends in the forward and distal directions 62 and 67 relative to a reference vector 141 that extends normal to the junction point 139 in the forward direction 62, the reference vector 141 being coplanar with the mid-plane 52. The bulkhead plane 140 thereby defines a slope angle θ relative to the reference vector 141, the slope angle θ extending distal to the reference vector 141. In some embodiments, the slope angle θ is within a range of 10 degrees to 60 degrees inclusive; in some embodiments, the slope angle θ is within a range of 15 degrees to 50 degrees inclusive; in some embodiments, the slope angle θ is within a range of 20 degrees to 40 degrees inclusive.

In some embodiments, one or more valve actuators 138 extend through the base portion 46 for routing flows into and out of the catheter assembly 30 and for isolating input ports 134 through which devices are inserted. Where a plurality of valve actuators 138 are implemented, the valve actuators 138 may be configured to rotate in the same lineal direction (as opposed to rotational direction). For example, the plurality of valve actuators 138 may include levers 144 or other indicators that point in the same direction when in a flow enabling configuration, regardless of whether the valve actuator 138 extends from housing portion 42a or housing portion 42b. In the depicted embodiment, all of the levers 144 of the valve actuators 138 point in the rearward direction 64 when in a flow-enabling or open configuration (FIGS. 2 and 4). Likewise, all of the levers 144 may be oriented to point, for example, downward when the valve actuators 138 are in a flow-isolation or closed configuration (not depicted). The corresponding rotational directions are depicted with rotation arrows 146 proximate the valve actuators 138 in FIGS. 2 and 4, depicting the rotational direction from the closed configuration to the open configuration. To effect the depicted lineal direction pointing, the rotational direction of the valve actuators 138 extending through the housing portion 42a rotate in an opposite direction from the valve actuators 138 extending through the housing portion 42b. In the depicted embodiment, the valve actuators 138 on the housing portion 42a rotate clockwise (FIG. 2), whereas the valve actuators 138 on the housing portion 42b rotate counterclockwise (FIG. 4).

The depictions of FIGS. 2 and 3 present a human hand 160 in phantom, the hand 160 having a thumb T and phalanges P identified as an index finger I, a middle finger M, a ring finger R, and a little finger L. In FIG. 2, a catch finger 162 is disposed in the catch 102, and an actuation finger 164 is positioned on the finger rest 108. In FIGS. 2 and 3, the catch finger 162 is the middle finger M, but any of the phalanges P may be selected as the catch finger 162. The actuation finger 164 is so-named because it is the finger that actuates the push button actuator(s) 126. In FIG. 2, the actuation finger 164 is the index finger I, but this is non-limiting, as the middle finger M or ring finger R may also be chosen to perform the actuation. Furthermore, more than one finger may be simultaneously implemented as actuation the fingers 164 (e.g., the index finger I and middle finger M).

Functionally, the curved body portion 48 of the housing 42 may be shaped to ergonomically fit the curve of a hand palm. The housing 42 enables performing all the functions of operation without need for changing the gripping posture of the hand. By reducing the junction dimension 90 of the catheter steering handle 32 at the transition portion 82, the thumb T and the catch finger 162 disposed within the catch 102 are brought into closer proximity than with conventional steering handles. Hand fatigue is thereby reduced when gripping the body portion 48 with the catch finger 162 positioned in the catch 102. Fatigue is also reduced while the thumb T is actuating the thumb lever 122, again because of the closer proximity of the thumb to the catch finger 162 when gripping the body portion 48. The slope angle θ of the bulkhead 132 avoids or reduces interference of the tubes (not depicted) that extend from the input ports 134 with placement of the hand 160.

The dimensions 116 and 119 of the catch 102 and ratios thereof are configured to capture the catch finger 162. That is, the catch 102 is configured so that the catheter steering handle 32 can hang or dangle over the catch finger 162. In some embodiments, a center of gravity 166 of the handle 32 is located proximate or within the base portion 46, such that the base portion 46 aligns vertically below the catch finger 162 when the handle 32 is not grasped (FIG. 9). In some embodiments, the distal extension of the catheter 34 and the cable 120 equalizes the balance of the catheter steering handle 32 so that the handle 32 may be balanced on the catch finger 162 without need for grasping the handle 32. Accordingly, by positioning the catch finger 162 within the catch 102, the operator may rest or relieve the hand (e.g., by loosening the grip or flexing the hand) while the catheter steering handle 32 hangs from the catch finger 162, as described attendant to FIGS. 8 through 10.

Figure 1B:
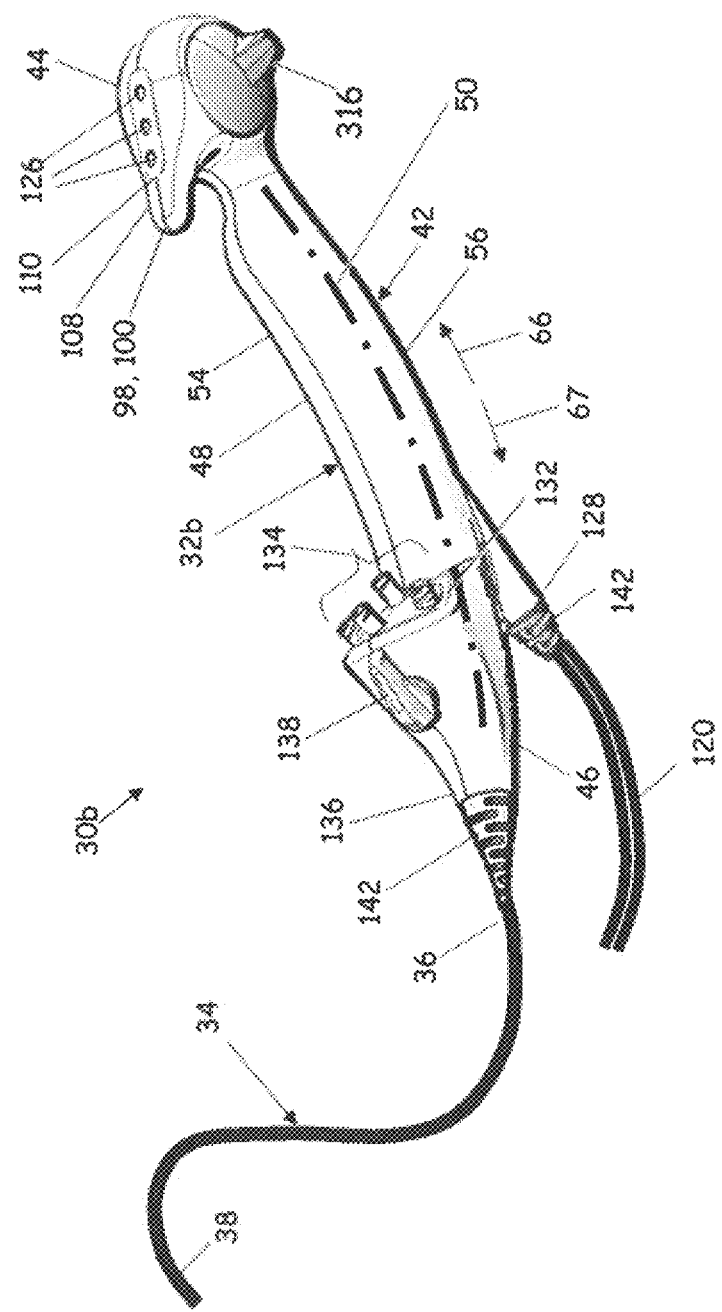

The steering handle 32b is depicted at FIGS. 1B, 6B and 7B. While FIGS. 2 through 5 depict only the steering handle 32a, the ergonomic aspects discussed attendant to FIGS. 2 through 5 apply equally to the steering handle 32b. One difference between the steering handle 32a and 32b is the geometry of the protrusion 98 and forward face 110. The protrusion 98 of steering handle 32b extends further in the forward direction 62 than does the protrusion 98 of steering handle 32a. Also, the forward face 110 of the steering handle 32b defines a linear tangential slope 152, whereas the forward face 110 of the steering handle 32a defines a concavity 154.

Functionally, the geometries of the forward faces 110 of the steering handles 32a and 32b each provide their own advantages. The convexity 154 of the forward face 110 of the steering handle 32a provides a tactile reference for the operator as to where the buttons 126 are on the forward face 110. The tangential linear slope 152 of the forward face 110 of the steering handle 32b provides a greater length for operators who prefer to use a pair of phalanges P on the forward face 110 during operation of the buttons 126.

Referring to FIGS. 8 through 10, dexterous operation of the catheter steering handle 32 is depicted according to an embodiment of the disclosure. The catheter steering handle 32 may be grasped with all the fingers (phalanges P and thumb T) as depicted in FIGS. 2 and 8. Upon gripping the catheter steering handle 32, the catch finger 162 is positioned within the catch 102. When executing the steering function, the operator grips the catheter steering handle 32 between the thumb T and the phalanges P (FIG. 8). The selected catch finger 162 is inserted into the catch 102 and the thumb T is positioned on the thumb lever 124. While the middle finger M, is depicted in FIGS. 8 through 10 as the catch finger 162, any of the phalanges P may be utilized as the catch finger 162. The selected actuation finger(s) 164 may be positioned on the finger rest 108. The distal end portion 38 of the steerable catheter 34 is flexed by articulating the thumb lever 124 forward and back with the thumb T. The actuation finger(s) 164 may be slid upward and onto the push button actuator(s) 126 to position the actuation finger(s) 164 for actuation of the push button actuator(s) 126.

To relax the hand 160, the operator can release the grip on the catheter steering handle 32 while maintaining the position of the catch finger 162 within the catch 102. In this way, the catheter steering handle 32 hangs from the catch finger 162 while the hand 160 is flexed or relaxed (FIGS. 9 and 10). Release of the grip can entail removing the thumb T from the thumb lever 124 (FIG. 9), or by leaving the thumb T engaged with the thumb lever 124 (FIG. 10). In the latter configuration, the operator may continue to manipulate or maintain the orientation of the distal end portion 38 of the steerable catheter 34 while flexing the hand 160. The hand 160 is also depicted in phantom in FIGS. 2 and 3. While the depicted hand 160 is a right hand, it is understood that either a left hand or a right hand may be utilized for the depicted catheter steering handles 32.

The center of gravity 166 of the handle 32 is depicted in FIG. 9 as being proximate the base portion 46, with the center of gravity 166 being centered below the catch 102 and catch finger 162 along a vertical axis 168, where the vertical axis 168 is aligned with gravity. The distal extension of the catheter 34 and the cable 120 may also equalize the balance of the catheter steering handle 32 so that the handle 32 is balanced on the catch finger 162 without need for grasping the handle 32. As such, the handle naturally suspends itself from the catch finger 162 when the hand is flexed or relaxed, thereby requiring no effort on the part of the operator to maintain the orientation of the handle 32 when at rest.

The finger rest 108 of the protrusion 98 provides a zone on the head portion 44 where the actuation finger can safely perch during periods when there is no push button actuation. The operator does not need to maintain the actuating finger extended away from the head portion 44 between actuations to avoid inadvertent actuation of the push button actuators, or rest the actuation finger at a remote location on the head portion 44. The finger rest 108 is also at a location on the head portion 44 that is at a known and close proximity to the push button actuator(s) 126 when resting the actuation finger.

In some embodiments, the foregoing methods of relieving hand fatigue while operating a catheter steering handle is provided as instructions on a tangible, non-transitory medium. Non-limiting examples of a tangible, non-transitory medium include a paper document and computer-readable media including compact disc and magnetic storage devices (e.g., hard disk, flash drive, cartridge, floppy drive). The computer-readable media may be local or accessible over the internet. The instructions may be complete on a single medium, or divided among two or more media. For example, some instructions may be written on a paper document that instruct the user to access one or more of the steps of the method over the internet, the internet-accessible steps being stored on a computer-readable medium or media. The instructions may be in the form of written words, figures, and/or video presentations.

The following references are hereby incorporated by reference herein in their entirety except for patent claims and express definitions contained therein: U.S. Provisional Patent Application No. 62/868,271, filed Jun. 28, 2019 and owned by the assignee of the present application; International Patent Application No. entitled "Efficient Multi-Functional Endoscopic Instrument" to Altshuler, et al., filed on even date and owned by the owner of the present application; International Application No. PCT/US Serial No. 19142491 to Altshuler, et al., filed Jul. 18, 2019 and owned by the owner of the present application; U.S. Pat. No. 9,775,675 to Irby, III. Any incorporation by reference of documents herein is limited such that no subject matter is incorporated that is contrary to the explicit disclosure herein.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A steering handle for a catheter, comprising:
a housing including a body portion defining a handle axis that is curvilinear and a head portion and a base portion separated by the body portion along the handle axis, the housing defining a mid-plane that is coplanar with the handle axis and passes through a forward side and a rearward side of the housing; and
wherein the housing defines a transition portion at a junction between the body portion and the head portion, the head portion and the transition portion defining a catch on the forward side of the housing at the mid-plane, the catch defines a hook profile configured for insertion of a a phalange (P) of a hand and formed by a protrusion that extends in a forward direction from the head portion and partially over the body portion, and at least a portion of the protrusion provides a finger rest.

2. The steering handle of claim 1, wherein at least one push button actuator is disposed proximate the finger rest.

3. The steering handle of claim 1, wherein at least one push button actuator is disposed on the head portion proximate the protrusion.

4. The steering handle of claim 1, wherein:
the catch defines an opening at the mid-plane, the opening being defined along a reference line that defines a minimum opening dimension from the forward side of the body portion of the handle to a reference point and a distal end portion of the protrusion; and
the catch defines a depth at the mid-plane, the depth being defined as a maximum depth dimension from the reference line to the hook profile that is perpendicular to the reference line.

5. The steering handle of claim 4, wherein the maximum depth dimension is within a range of 13 millimeters to 28 millimeters inclusive.

6. The steering handle of claim 1, wherein the housing defines a cross-section about the handle axis at the transition portion that defines a junction dimension coplanar with the mid-plane that is reduced relative to the head portion and the body portion at the mid-plane immediately adjacent the transition portion.

7. The steering handle of claim 1, wherein the rearward side of the body portion defines a convex profile at the mid-plane and the forward side of the body portion defines a concave portion at the mid-plane.

8. The steering handle of claim 7, wherein at least one of the convex profile and the concave profile defines a radius in a range of 100 millimeters to 500 millimeters inclusive.

9. The steering handle of claim 1 comprising a thumb lever coupled to the head portion, the thumb lever being rotatable about a lateral axis that is orthogonal to the mid-plane.

10. The steering handle of claim 9, wherein the thumb lever extends in a rearward direction and parallel to the mid-plane.

11. The steering handle of claim 1, wherein the base portion includes a bulkhead.

12. The steering handle of claim 11, wherein an exterior surface of the bulkhead is centered about a bulkhead plane, the bulkhead plane intersecting the body portion of the handle at the forward side of the housing to define a junction point on the mid-plane, the bulkhead plane defining an acute slope angle that extends distally from a reference vector that is normal to the forward side of the housing at the junction point.

13. The steering handle of claim 12, wherein the acute slope angle is within a range of 10 degrees to 60 degrees inclusive.

14. The steering handle of claim 1, further comprising at least one valve actuator extending through the base portion.

15. The steering handle of claim 1, wherein a center of gravity of the steering handle is located proximate the base portion and centered below the catch along a vertical axis, where the vertical axis is aligned with gravity.

16. A catheter assembly including the steering handle of claim 1, the catheter assembly including a steerable catheter and an electrical cable, each coupled to the base portion of the steering handle and configured to equalize the balance of the steering handle.

\* \* \* \* \*